(12) United States Patent
Chen et al.

(10) Patent No.: US 9,700,315 B2
(45) Date of Patent: *Jul. 11, 2017

(54) LINEAR CUTTING STAPLER

(75) Inventors: Wangdong Chen, Jiangsu (CN); Kaifen Fu, Jiangsu (CN); Jing Zhou, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 711 days.

This patent is subject to a terminal disclaimer.

(21) Appl. No.: 13/993,997

(22) PCT Filed: Nov. 29, 2011

(86) PCT No.: PCT/CN2011/083114
§ 371 (c)(1),
(2), (4) Date: Jun. 13, 2013

(87) PCT Pub. No.: WO2012/079455
PCT Pub. Date: Jun. 21, 2012

(65) Prior Publication Data
US 2013/0264370 A1 Oct. 10, 2013

(30) Foreign Application Priority Data
Dec. 16, 2010 (CN) .......................... 2010 1 0592492

(51) Int. Cl.
*A61B 17/072* (2006.01)
*A61B 90/00* (2016.01)

(52) U.S. Cl.
CPC ...... *A61B 17/072* (2013.01); *A61B 17/07207* (2013.01); *A61B 90/03* (2016.02);
(Continued)

(58) Field of Classification Search
CPC . A61B 17/072; A61B 17/07207; A61B 19/30; A61B 2017/07278; A61B 2017/07285
(Continued)

(56) References Cited

U.S. PATENT DOCUMENTS 4,383,634 A * 5/1983 Green .................. A61B 17/072
227/135
4,892,244 A 1/1990 Fox et al.
(Continued)

FOREIGN PATENT DOCUMENTS

CN 2764312 Y 3/2006
CN 101675895 A 3/2010
(Continued)

OTHER PUBLICATIONS

Extended European Search Report corresponding to Application No. 11849592.8-1654/2653114, PCT/CN2011/083114; Issued: Sep. 18, 2015.
(Continued)

*Primary Examiner* — Hemant M Desai
*Assistant Examiner* — Valentin Neacsu
(74) *Attorney, Agent, or Firm* — Cantor Colburn LLP (57) ABSTRACT

A linear cutting stapler includes an upper jaw and a lower jaw capable of closing or opening relative to each other. A staple cartridge is disposed at a distal end of the lower jaw. The lower jaw is U-shaped, and has a staple driving rod and a blade driving rod slidably disposed therein. The linear cutting stapler further includes a safety mechanism which includes an engagement member. A notch fitting the engagement member is disposed on a bottom surface of the staple driving rod. The safety mechanism further includes a floating block which is displaceable in the lower jaw in an up-down direction perpendicular to the length direction of the lower jaw. When the floating block is pressed against the
(Continued)

staple cartridge or an anvil, a top end of the engagement member is driven to displace in the up-down direction, thus the engagement member is separated from the notch.

12 Claims, 14 Drawing Sheets

(52) U.S. Cl.
CPC .............. *A61B 2017/07278* (2013.01); *A61B 2017/07285* (2013.01)

(58) Field of Classification Search
USPC ...................................................... 227/175.2
See application file for complete search history.

(56) References Cited

U.S. PATENT DOCUMENTS

| | | | | |
|---|---|---|---|---|
| 5,129,570 | A * | 7/1992 | Schulze | A61B 17/07207 227/175.2 |
| 5,156,315 | A * | 10/1992 | Green | A61B 17/07207 227/178.1 |
| 5,307,976 | A * | 5/1994 | Olson | A61B 17/07207 227/175.3 |
| 5,332,142 | A * | 7/1994 | Robinson | A61B 17/07207 227/175.2 |
| 5,413,268 | A * | 5/1995 | Green | A61B 17/07207 227/176.1 |
| 5,445,304 | A * | 8/1995 | Plyley | A61B 17/07207 227/176.1 |
| 5,458,279 | A * | 10/1995 | Plyley | A61B 17/072 227/176.1 |
| 5,673,842 | A * | 10/1997 | Bittner | A61B 17/07207 227/175.2 |
| 5,678,748 | A * | 10/1997 | Plyley | A61B 17/072 227/175.4 |
| 5,911,352 | A * | 6/1999 | Racenet | A61B 17/07207 227/175.1 |
| 5,988,479 | A | 11/1999 | Palmer | |
| 7,055,730 | B2 * | 6/2006 | Ehrenfels | A61B 17/07207 227/175.4 |
| 7,334,717 | B2 * | 2/2008 | Rethy | A61B 17/07207 227/175.1 |
| 9,433,414 | B2 * | 9/2016 | Chen | A61B 17/07207 |
| 2004/0007608 | A1 * | 1/2004 | Ehrenfels | A61B 17/07207 227/176.1 |
| 2005/0159778 | A1 * | 7/2005 | Heinrich | A61B 17/072 606/216 |
| 2007/0145095 | A1 * | 6/2007 | Heinrich | A61B 17/072 227/175.1 |
| 2009/0134199 | A1 * | 5/2009 | Heinrich | A61B 17/072 227/178.1 |
| 2009/0261145 | A1 * | 10/2009 | Heinrich | A61B 17/072 227/180.1 |
| 2010/0065604 | A1 * | 3/2010 | Weng | A61B 17/07207 227/175.2 |
| 2010/0072251 | A1 * | 3/2010 | Baxter, III | A61B 17/07207 227/175.2 |
| 2010/0193570 | A1 * | 8/2010 | Ehrenfels | A61B 17/07207 227/176.1 |

FOREIGN PATENT DOCUMENTS

| | | |
|---|---|---|
| CN | 101756738 A | 6/2010 |
| CN | 101797174 A | 8/2010 |
| CN | 102068290 A | 5/2011 |
| CN | 202122595 U | 1/2012 |
| EP | 2163209 A1 | 3/2010 |
| JP | 2-177951 A | 7/1990 |
| JP | 5-38341 A | 2/1993 |
| JP | 6-121798 A | 5/1994 |
| JP | 9-164144 A | 6/1997 |
| JP | 2007-252952 A | 10/2007 |
| JP | 2010-63895 A | 3/2010 |
| JP | 2010-69307 A | 4/2010 |
| JP | 2010-240464 A | 10/2010 |
| WO | 9210976 A1 | 7/1992 |

OTHER PUBLICATIONS

International Search Report for International Application No. PCT/CN2011/083114, mailed Mar. 8, 2012, with English translation.
Notice of Grounds of Rejection for Japanese Patent Application No. 2013-543506, mailed Apr. 22, 2014, with English translation.

* cited by examiner

LINEAR CUTTING STAPLER

The present application is the US national phase of International Application No. PCT/CN2011/083114 filed on Nov. 29, 2011, which claims the benefit of priority to Chinese Patent Application No. 201010592492.X titled "LINEAR CUTTING STAPLER" and filed with the State Intellectual Property Office on Dec. 16, 2010, the entire disclosure of which is incorporated herein by reference.

FIELD OF THE INVENTION

The present application relates to a linear cutting stapler, which belongs to the technical field of medical instruments.

BACKGROUND OF THE INVENTION

Linear cutting staplers are widely used in surgical operations for wound closure, and internal tissue closure and excision. A typical linear cutting stapler as disclosed in U.S. Pat. No. 5,129,570 performs two functions of stapling and cutting, to remove the redundant tissue while stapling the wound. This kind of linear cutting stapler generally includes two jaws (i.e., an upper jaw and a lower jaw), a closing handle for closing the upper jaw and the lower jaw, a staple anvil and a staple cartridge arranged opposite to each other at the front ends of the upper jaw and lower jaw respectively, a firing piece and a cutter which are arranged in the staple cartridge and are moveable synchronously relative to the staple cartridge, and a push button for driving movement of the firing piece and the cutter. Staples are arranged in the staple cartridge. The firing piece pushes a staple pusher successively and pushes the staples towards the staple anvil. The cutter cuts off the tissue between the staple cartridge and the staple anvil.

In clinical application, multiple times of stapling and cutting tissues are often required, and thus the staple cartridge is required to be replaced for many times in an operation. When no staple cartridge is loaded, the push button can be pushed forwards arbitrarily, and then the cutter may be pushed out. This may cause serious consequence as arising from only cutting without stapling. Accordingly, a safety mechanism is provided in the linear cutting staplers in the prior art.

The U.S. Pat. No. 5,129,570 discloses a safety mechanism, in which a safety block with a cutter passage and a staple pushing bar passage is provided in the middle portion of the instrument, and a leaf spring is provided under the cutter. When the instrument is in an opened position, i.e., the upper jaw and the lower jaw are not closed, the leaf spring lifts the cutter upwards, so that the cutter cannot pass through the cutter passage, thereby playing the role of safety. After the staple cartridge is loaded in the instrument, and the two upper and lower jaws are closed, the staple cartridge forces the top portion of the cutter, so that the cutter overcomes the elastic force of the leaf spring and returns to be in alignment with the cutter passage. At this moment, the safety mechanism is deactivated and the instrument can eject the cutter.

The U.S. Pat. No. 7,055,730 discloses another safety mechanism, in which a safety block with a cutter pushing bar passage and a staple pushing bar passage is provided in the middle portion of the instrument, with the safety block being rotatable around the instrument under the action of the torsion spring. When the instrument is in an opened position, i.e., the upper jaw and the lower jaw are not closed, the safety block twists such that neither the staple pushing bar nor the cutter pushing bar are allowed to pass through their passages, thereby playing the role of safety. After the staple cartridge is loaded in the instrument, and the upper jaw and the lower jaw are closed, the staple cartridge forces the safety block such that the safety block overcomes the elastic force of the torsion spring and returns into the normal position. That is, the staple pushing bar and the cutter pushing bar align with their own passages on the safety block respectively, so that both the staple pushing bar and the cutter pushing bar are allowed to pass through the safety block. At this moment, the safety mechanism is deactivated and the instrument can eject the cutter.

All of the above structures are complicated, and difficult to be manufactured and assembled, as well as costly.

SUMMARY OF THE INVENTION

An object of the present application is to provide a linear cutting stapler having a safety mechanism with simple structure.

The object of the present application will be implemented by the following technical solutions.

A linear cutting stapler includes an upper jaw and a lower jaw capable of being closed or opened relative to each other. A staple cartridge is provided at a distal end of the lower jaw. The lower jaw has a U shape with a staple pushing bar and a cutter pushing bar slidably provided therein. The linear cutting stapler further includes a safety mechanism including an engaging member. A bottom surface of the staple pushing bar is provided with a notch to be engaged with the engaging member. The safety mechanism further includes a floating block displaceable in the lower jaw in an up-down direction perpendicular to a length direction of the lower jaw such that when the floating block abuts against the staple cartridge or a staple anvil to drive the top end of the engaging member to displace in the up-down direction perpendicular to the length direction of the lower jaw, the engaging member is disengaged from the notch.

Further, the bottom end of the floating block is connected to the top end of the engaging member, and the bottom end of the engaging member is connected to the lower jaw. A first through slot and a second through slot for the staple pushing bar and the cutter pushing bar to pass through respectively are provided on the floating block in an axial direction.

Still further, a protrusion to be pressed by the staple cartridge is provided at a distal end of the floating block. By pressing the protrusion, the staple cartridge further drives the top end of the engaging member to displace in the up-down direction perpendicular to the length direction of the lower jaw, so that the engaging member is disengaged from the notch.

Still further, a protrusion to be pressed by the staple anvil is provided at a proximal end of the floating block. By pressing the protrusion, the staple anvil further drives the top end of the engaging member to displace in the up-down direction perpendicular to the length direction of the lower jaw, so that the engaging member is disengaged from the notch.

Still further, the engaging member is a leaf spring with a bottom end welded to the inner wall of the lower jaw and a top end fixedly connected to the floating block.

Still further, the engaging member is an engaging block at a bottom portion of the floating block. The top end of the engaging block is to be engaged with the notch. The bottom end of the engaging block is connected to the bottom surface of the lower jaw by a spring. When the floating block abuts against the staple cartridge or the staple anvil to drive the engaging member to displace in the up-down direction perpendicular to the length direction of the lower jaw, the bottom portion of the engaging member is disengaged from the notch.

Still further, the engaging block and the floating block are manufactured integrally.

Still further, the engaging member is connected to the center of the bottom surface of the lower jaw. The notch is correspondingly arranged at the center of the bottom surface of the staple pushing bar.

Still further, a protrusion is provided on each of the two sides of the floating block in an axial direction. A groove fitted with the protrusion is provided on each of the two inner side walls of the lower jaw. The protrusion is movable in the groove in the up-down direction perpendicular to the length direction of the lower jaw.

The present application has main beneficial effects, for example the linear cutting stapler has a simple structure, can be manufactured easily, and is safe and reliable, and as well as has a good market prospect.

Figure 1:
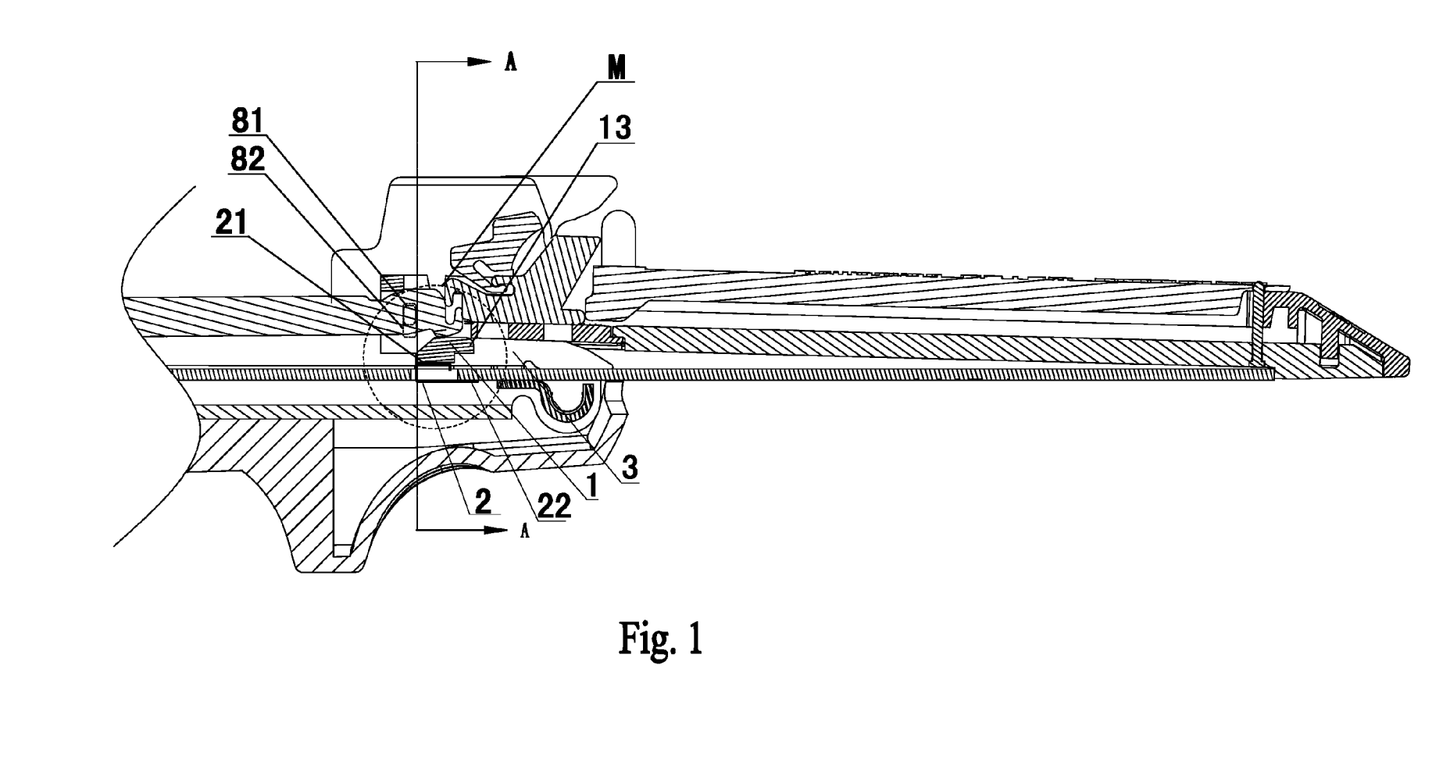
FIG. 1 is a schematic structural view of a lower jaw in a first embodiment, with a staple cartridge being not shown.
Figure 2:
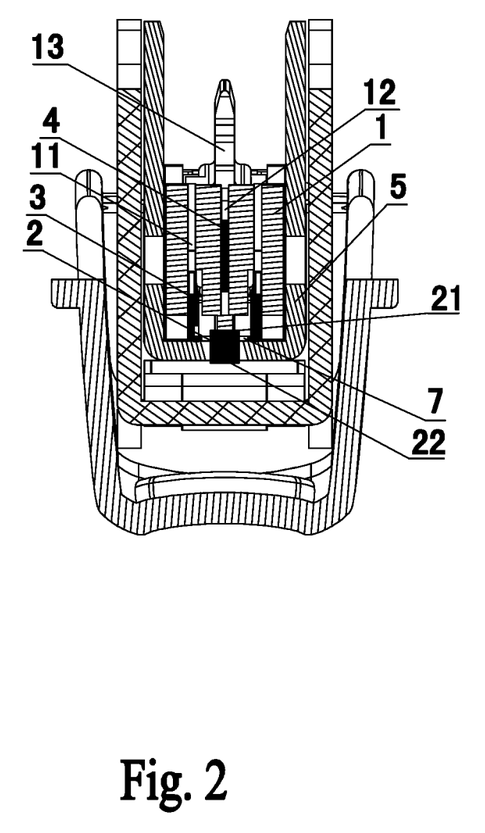
FIG. 2 is a cross sectional view taken along line A-A in FIG. 1.
Figure 3:
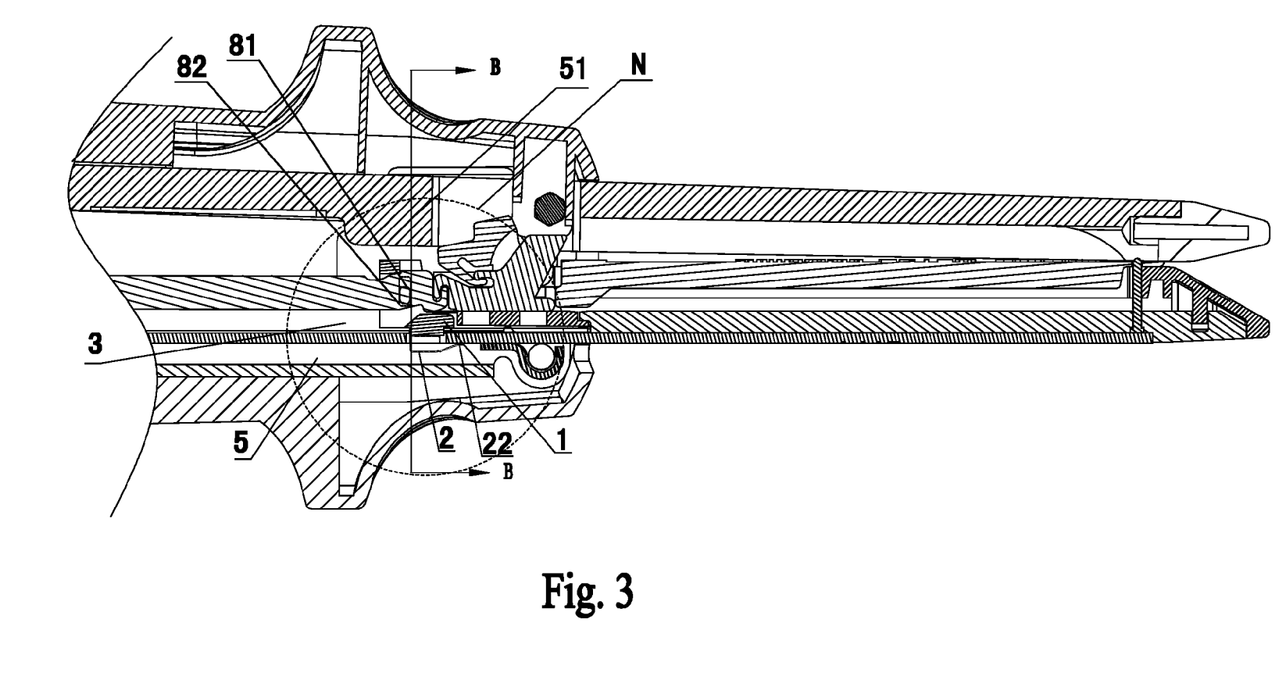
FIG. 3 is a partial schematic structural view of the linear cutting stapler in the first embodiment.
Figure 4:
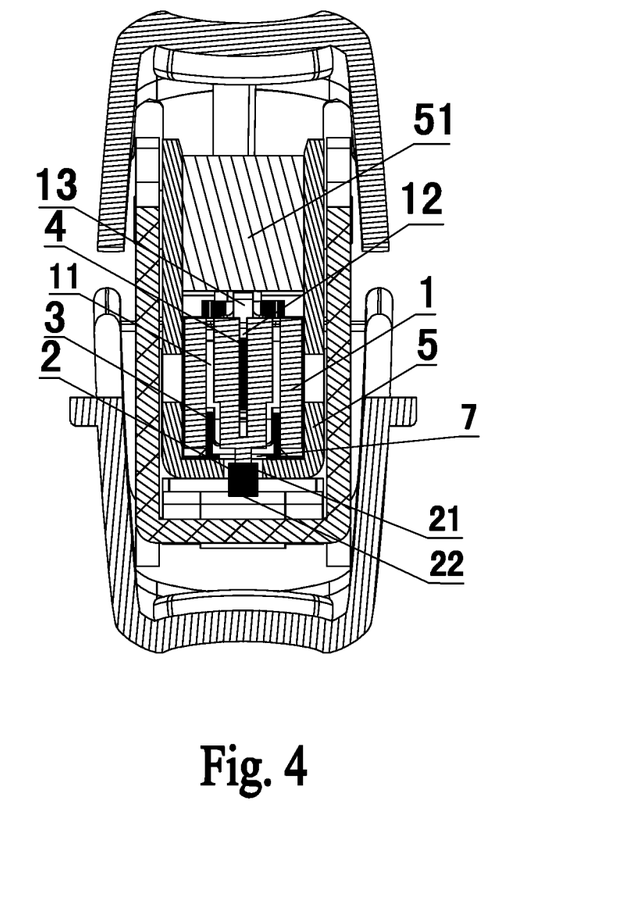
FIG. 4 is a cross sectional view taken along line B-B in FIG. 3.
Figure 5:
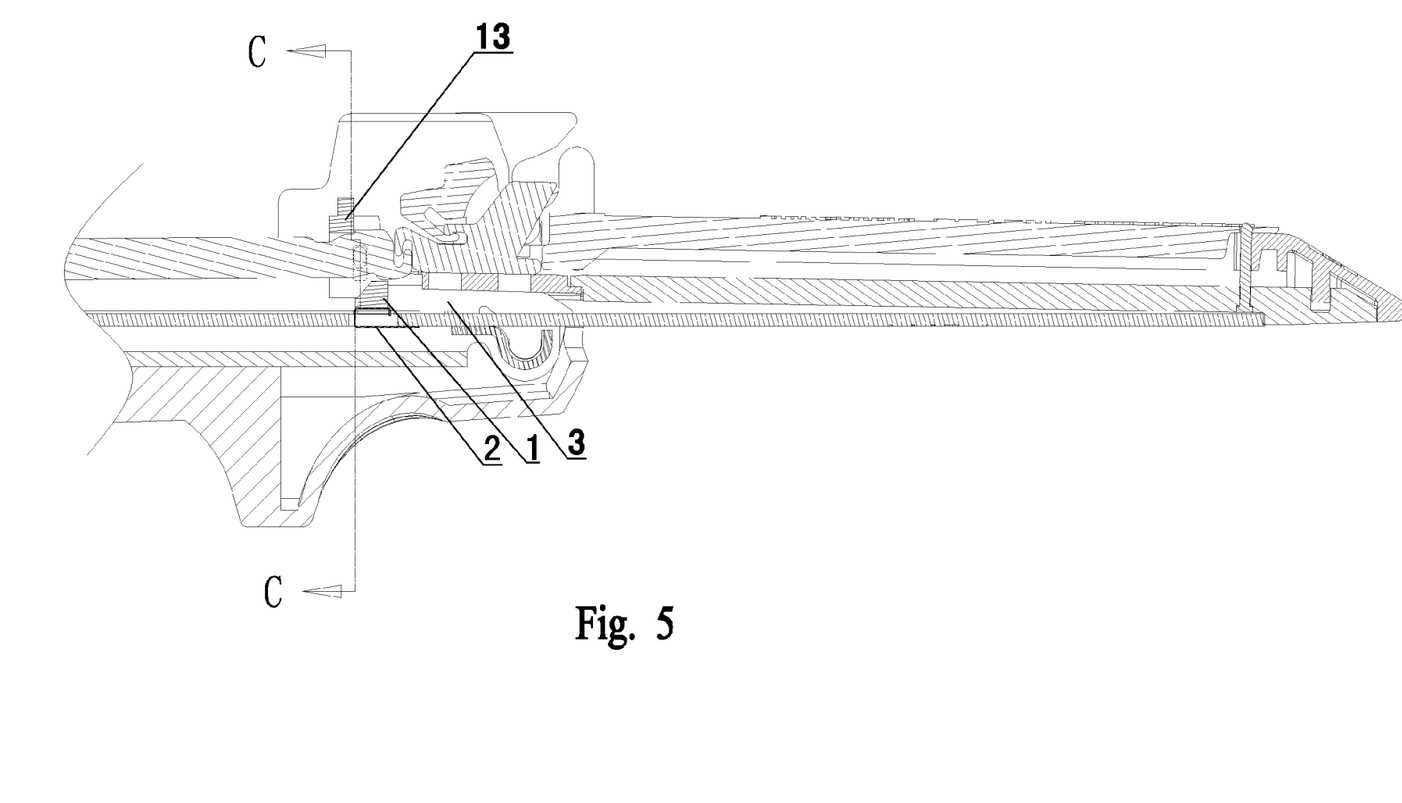
FIG. 5 is a schematic structural view of a lower jaw in a second embodiment, with the staple cartridge being not shown.
Figure 6:
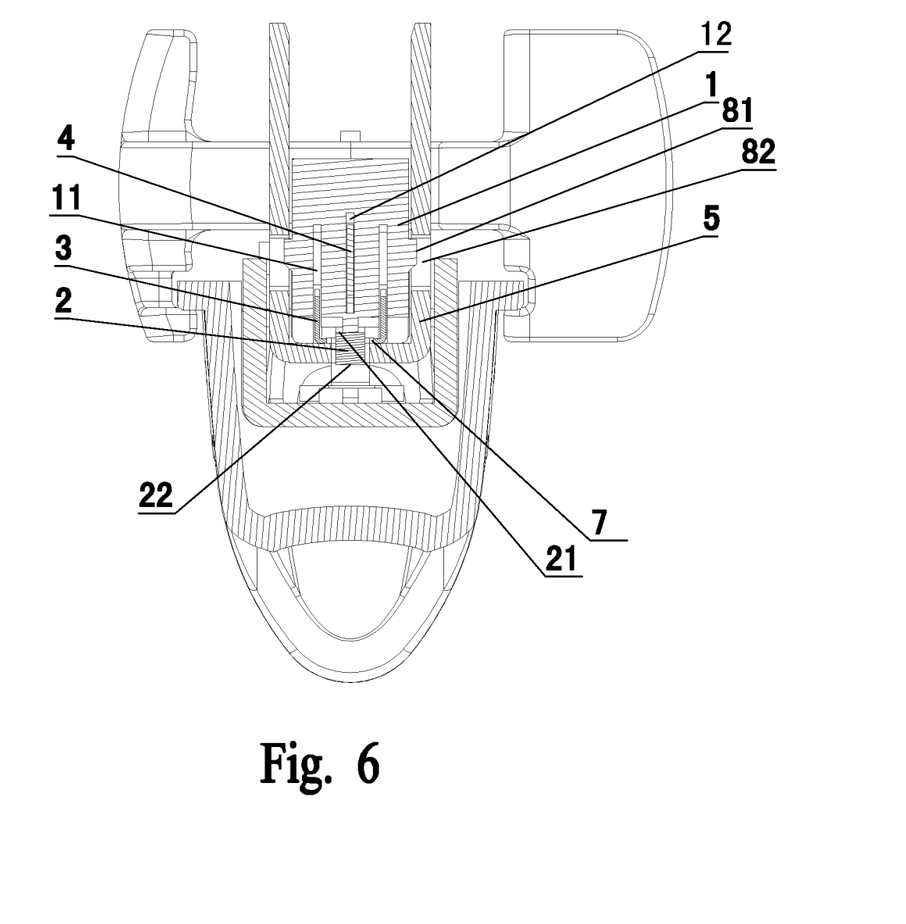
FIG. 6 is a cross sectional view taken along line C-C in FIG. 5.
Figure 7:
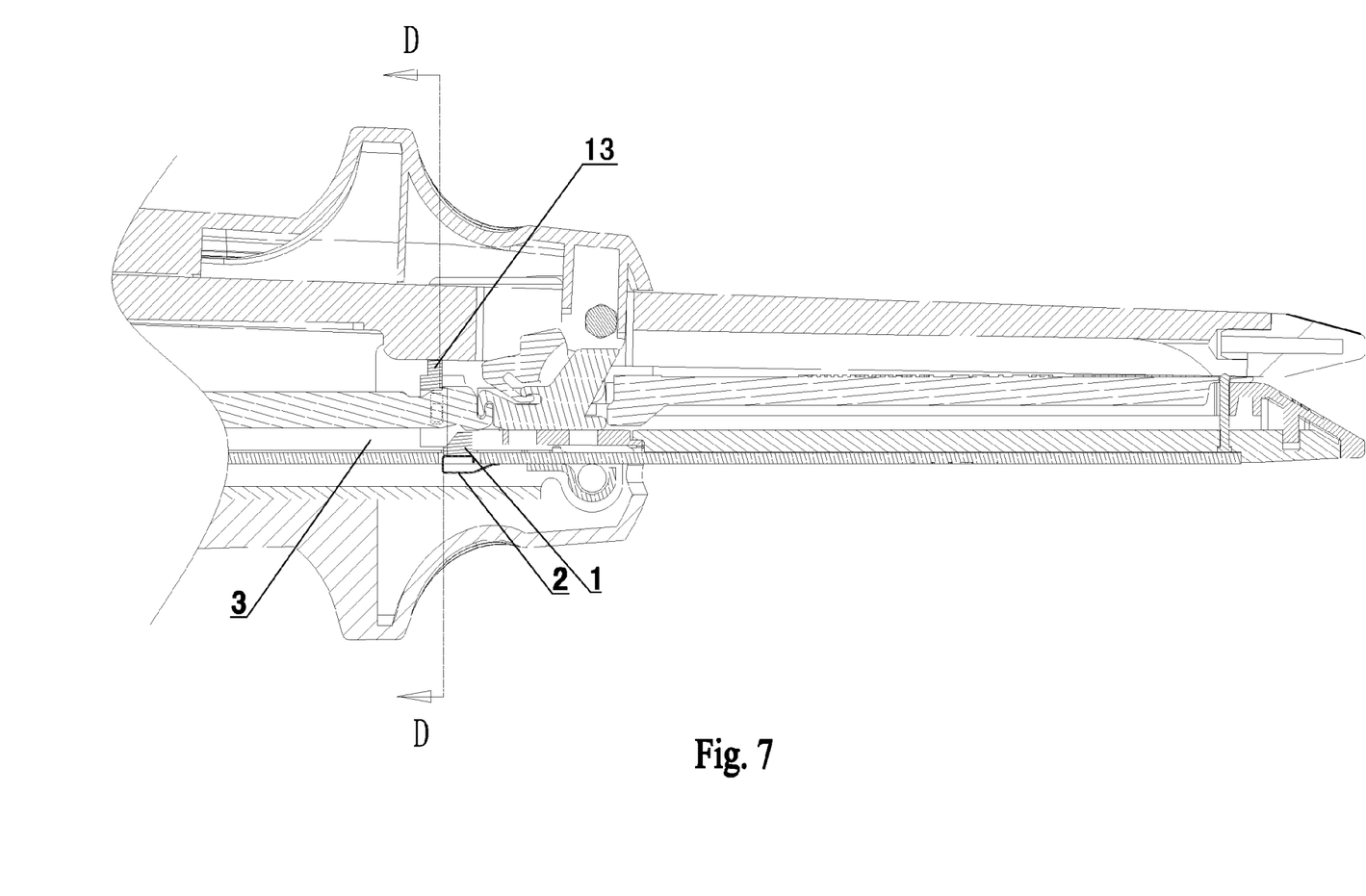
FIG. 7 is a partial schematic structural view of the linear cutting stapler in the second embodiment.
Figure 8:
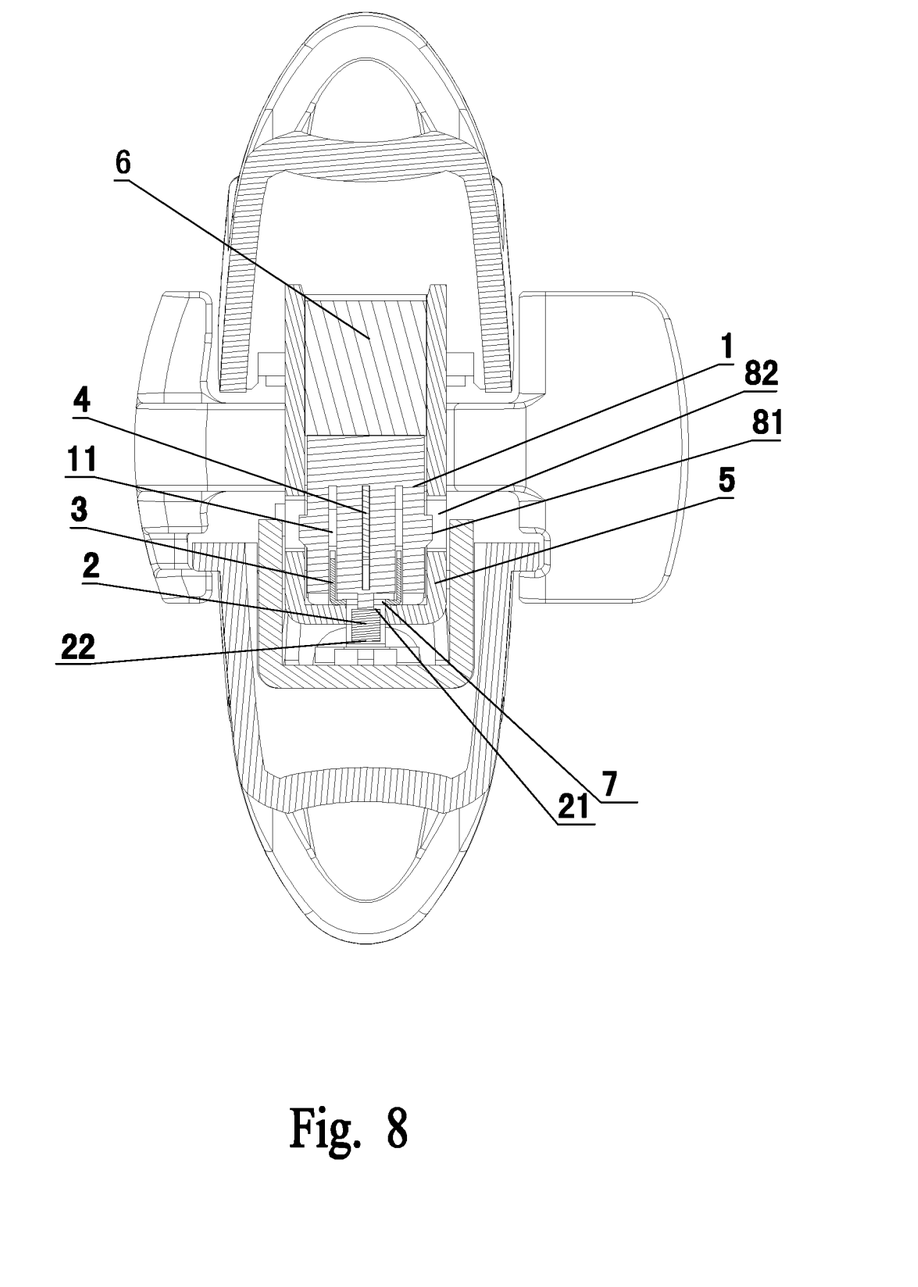
FIG. 8 is a cross sectional view taken along line D-D in FIG. 7.
Figure 9:
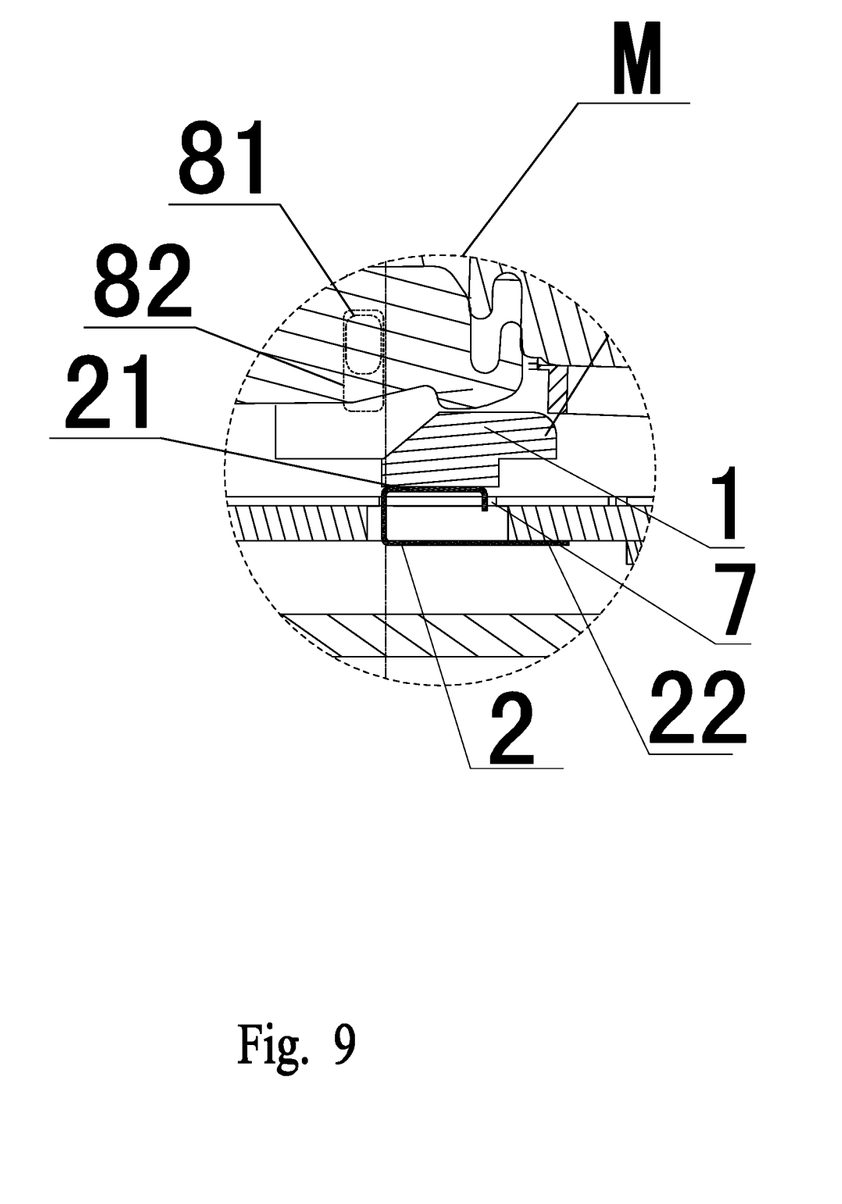
FIG. 9 is an enlarged view of portion M in FIG. 1.
Figure 10:
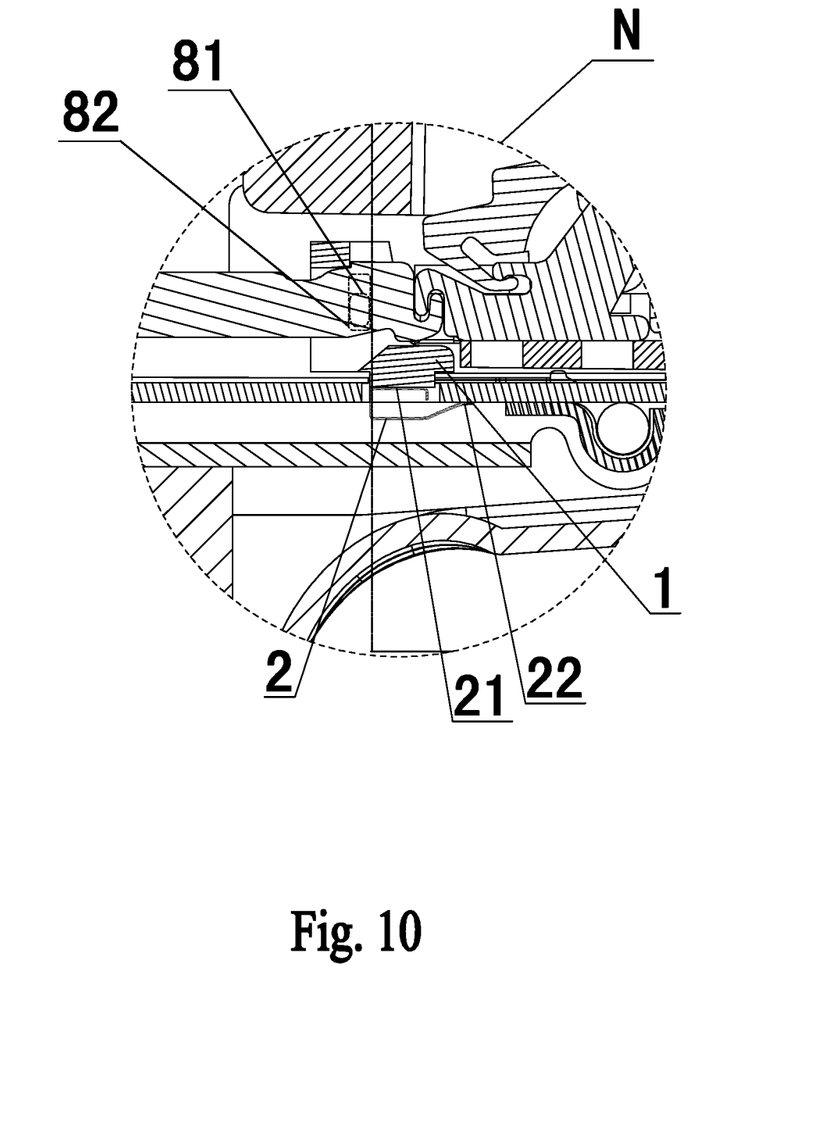
FIG. 10 is an enlarged view of portion N in FIG. 3.
Figure 11:
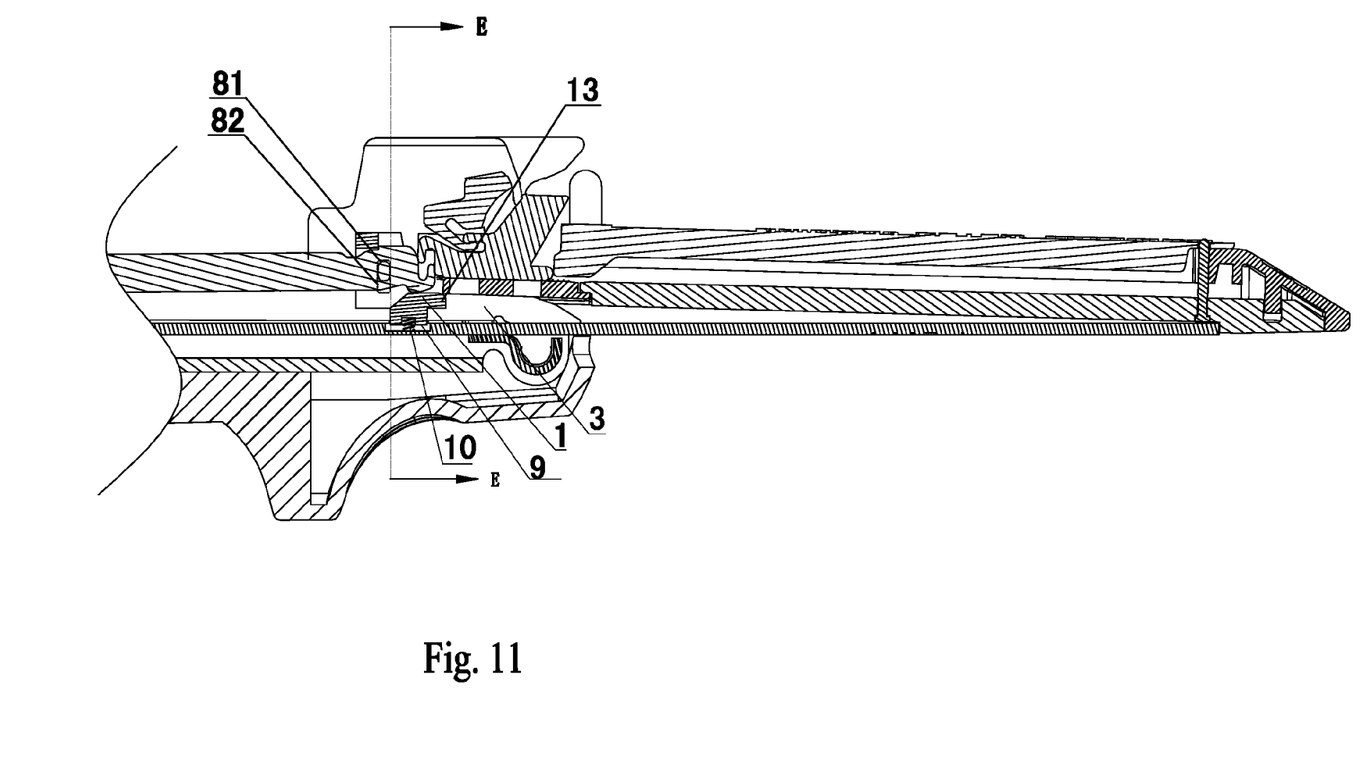
FIG. 11 is a schematic structural view of a lower jaw in a third embodiment, with the staple cartridge being not shown.
Figure 12:
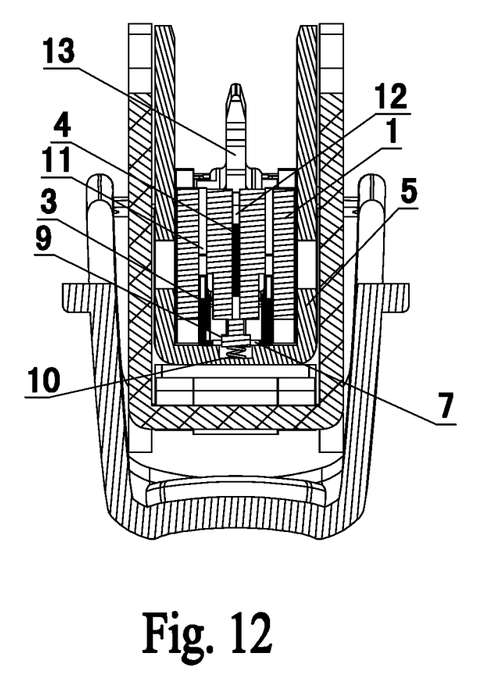
FIG. 12 is a cross sectional view taken along line E-E in FIG. 11.
Figure 13:
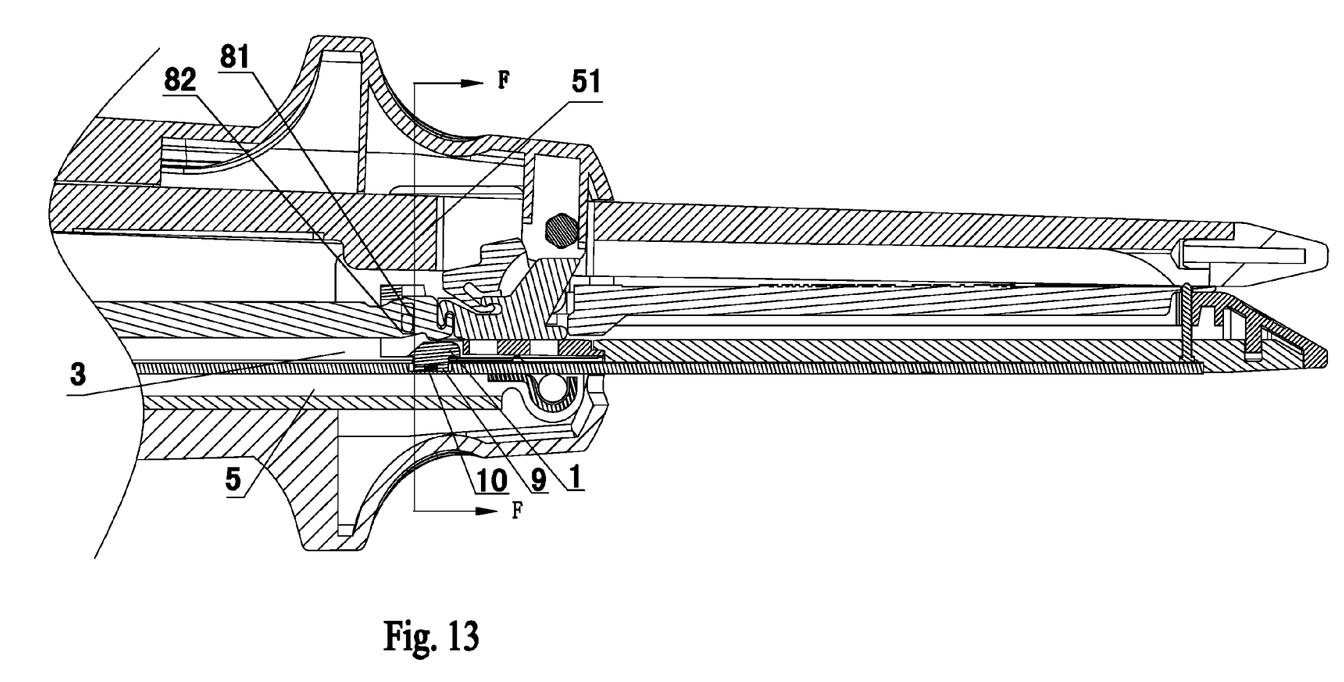
FIG. 13 is a partial schematic structural view of the linear cutting stapler in the third embodiment.
Figure 14:
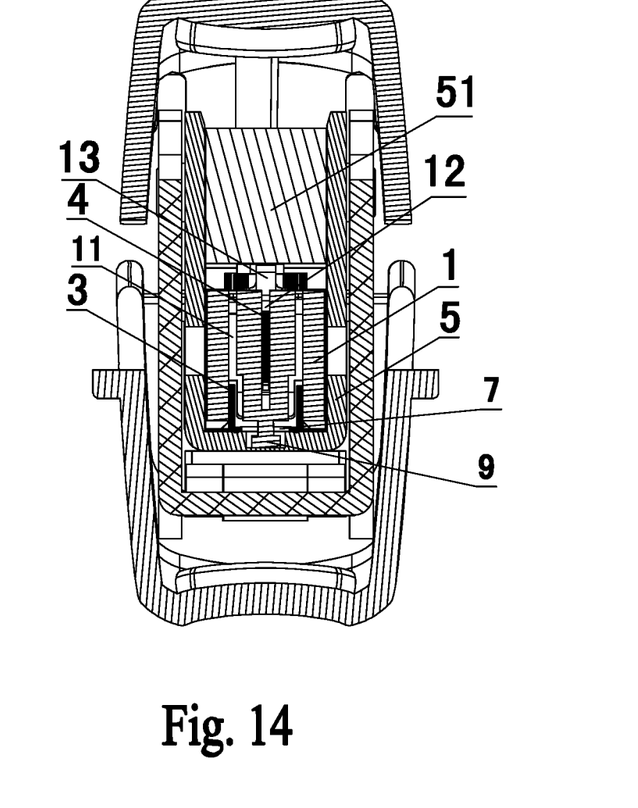
FIG. 14 is a cross sectional view taken along line F-F in FIG. 13.

Reference numerals in FIGS. 1 to 14

| 1: floating block; | 11: first through slot; |
|---|---|
| 12: second through slot; | 13: protrusion; |
| 2: leaf spring; | 3: staple pushing bar; |
| 4: cutter pushing bar; | 5: lower jaw; |
| 51: staple cartridge; | 6: staple anvil; |
| 7: notch; | 21: top end of leaf spring; |
| 22: bottom end of leaf spring; | 81: protrusion; |
| 82: groove; | 9: engaging block; |
| 10: spring. | |

DETAILED DESCRIPTION OF THE INVENTION

The present application provides a linear cutting stapler including an upper jaw and a lower jaw 5 capable of being closed or opened relative to each other. A staple cartridge 51 is arranged at a distal end of the lower jaw 5. The lower jaw 5 has a U shape with a staple pushing bar 3 and a cutter pushing bar 4 slidably arranged therein. The linear cutting stapler further includes a safety mechanism including an engaging member. The bottom surface of the staple pushing bar 3 is provided with a notch 7 to be engaged with the top end of the engaging member. The safety mechanism further includes a floating block 1 which may abut against the staple cartridge 51 or the staple anvil 6 and further drive the top end of the engaging member to displace in an up-down direction perpendicular to the length direction of the lower jaw 5 so as to cause the engaging member to be disengaged from the notch 7. A first through slot 11 and a second through slot 12 for the staple pushing bar 3 and the cutter pushing bar 4 to pass through respectively are arranged on the floating block 1 in an axial direction.

First Embodiment

As shown in FIGS. 1 to 4, 9 and 10, in the present application, the linear cutting stapler includes: an upper jaw, a U-shaped lower jaw 5; a staple pushing bar 3 and a cutter pushing bar 4 slidably arranged in the lower jaw 5; a safety mechanism including a leaf spring 2 and a floating block 1, with the bottom end 22 of the leaf spring 2 being welded to the center of the inner wall of the lower jaw 5 and the floating block 1 being connected to the top end 21 of the leaf spring 2. A first through slot 11 and a second through slot 12 for the staple pushing bar 3 and the cutter pushing bar 4 to pass through respectively are provided on the floating block 1 in an axial direction of the floating block 1. A notch 7 to be engaged with the top end 21 of the leaf spring 2 is provided at the center of the bottom surface of the staple pushing bar 3. A protrusion 13 to be pressed by the staple cartridge 51 is provided at a distal end of the floating block 1. A protrusion 81 is provided on each of the two sides of the floating block 1 in an axial direction, and a groove 82 fitted with the protrusion 81 is provided on each of the two inner side walls of the lower jaw 5. The protrusion 81 is movable in the groove 82 in the up-down direction perpendicular to the length direction of the lower jaw 5, so as to guide the floating block 1 to move in the up-down direction perpendicular to the length direction of the lower jaw 5. Of course, a groove (not shown) may also be provided at each of the two sides of the floating block 1, and a protrusion (not shown) fitted with the groove may be provided on each of the two inner side walls of the lower jaw 5.

The principle of operation of the present embodiment is described below. When the linear cutting stapler is not opened or the staple cartridge 51 not mounted, the floating block 1 floats upwards under the action of the leaf spring 2, and then the leaf spring 2 is engaged in the notch 7 of the bottom surface of the staple pushing bar 3, so that the staple pushing bar 3 cannot be pushed forwards, and thus the safety mechanism is activated. When the staple cartridge 51 is mounted to the lower jaw 5, and the upper jaw and the lower jaw are closed, the staple cartridge 51 presses the protrusion 13, so that the leaf spring 2 is pressed by the floating block 1 to move downwards. Then, the floating block 1 returns to a position which allows the staple pushing bar 3 and the cutter pushing bar 4 to pass through. Thus, the leaf spring 2 is disengaged from the notch 7. Therefore, the safety mechanism is deactivated.

Second Embodiment

As shown in FIGS. 5 to 8, in the present embodiment, the proximal end of the floating block 1 is provided with a protrusion 13 to be pressed by the staple anvil 6. Since other structures are the same as those in the first embodiment, the descriptions of those structures are not repeated here.

The principle of operation of the present embodiment is described below. When the linear cutting stapler is not opened or the staple cartridge 51 not mounted, the floating block 1 floats upwards under the action of the leaf spring 2, and then the leaf spring 2 is engaged in the notch 7 of the bottom surface of the staple pushing bar 3, so that the staple pushing bar 3 cannot be pushed forwards, and thus the safety mechanism is activated. When the staple cartridge 51 is mounted to the lower jaw 5, and the upper jaw and the lower jaw are closed, the staple anvil 6 presses the protrusion 13, so that the floating block 1 forces the leaf spring 2 to move downwards. Then, the floating block 1 returns to a position which allows the staple pushing bar 3 and the cutter pushing bar 4 to pass through. Thus, the leaf spring 2 is disengaged from the notch 7. Therefore, the safety mechanism is deactivated.

Third Embodiment

As shown in FIGS. 11 to 14, in the present embodiment, the engaging member is an engaging block 9 to be engaged with the notch 7. And the bottom end of the engaging block 9 is connected to the bottom surface of the lower jaw 5 by means of a spring 10. The engaging block 9 and the floating block 1 are manufactured integrally. Since other structures are the same as those in the first embodiment, the descriptions of those structures are not repeated here.

The principle of operation of the present embodiment is described below. When the linear cutting stapler is not opened or the staple cartridge 51 not mounted, the engaging block 9 floats upwards under the action of the spring 10, and the floating block 1 floats upwards as well under the action of the engaging block 9. The top end of the engaging block 9 is engaged in the notch 7 of the bottom surface of the staple pushing bar 3, so that the staple pushing bar 3 cannot be pushed forwards, and thus the safety mechanism is activated. When the staple cartridge 51 is mounted to the lower jaw 5, and the upper jaw and the lower jaw are closed, the staple cartridge 51 presses the protrusion 13, so that the floating block 1 urges the spring 10 to contract so as to drive the engaging block 9 to move downwards. Then, the floating block 1 returns to a position which allows the staple pushing bar 3 and the cutter pushing bar 4 to pass through. Thus, the engaging block 9 is disengaged from the notch 7. Therefore, the safety mechanism is deactivated.

Fourth Embodiment

In the present embodiment, the engaging member is an engaging block 9 with the top end of the engaging block 9 to be engaged with the notch 7, and the bottom end of the engaging block 9 connected to the bottom surface of the lower jaw 5 by means of a spring 10. The engaging block 9 and the floating block 1 are manufactured integrally. Since other structures are the same as those in the first embodiment, the descriptions of those structures are not repeated here.

The principle of operation of the present embodiment is described below. When the linear cutting stapler is not opened or the staple cartridge 51 not mounted, the engaging block 9 floats upwards under the action of the spring 10, and the floating block 1 floats upwards as well under the action of the engaging block 9. The top end of the engaging block 9 is engaged in the notch 7 of the bottom surface of the staple pushing bar 3, so that the staple pushing bar 3 cannot be pushed forwards, and thus the safety mechanism is activated. When the staple cartridge 51 is mounted to the lower jaw 5, and the upper jaw and the lower jaw are closed, the staple anvil 6 presses the protrusion 13, so that the floating block 1 urges the spring 10 to contract so as to drive the engaging block 9 to move downwards. Then, the floating block 1 returns to a position which allows the staple pushing bar 3 and the cutter pushing bar 4 to pass through. Thus, the engaging block 9 is disengaged from the notch 7. Therefore, the safety mechanism is deactivated.

The present application still includes a variety of embodiments. All the technical solutions formed by the equivalent variation or the equivalent modification fall into the protection scope of the present application.

The invention claimed is:

1. A linear cutting stapler, comprising a first half-section and a second half-section capable of being closed or opened relative to each other, with a staple cartridge being provided at an end of the second half-section, the second half-section having a U shape, and a staple pushing bar and a cutter pushing bar being slidably provided in the second half-section,
    wherein the linear cutting stapler further comprises a safety mechanism comprising an engaging member, a bottom surface of the staple pushing bar that is away from the first half-section is provided with a notch for engaging with the engaging member, and the engaging member is configured to engage with the notch at the bottom surface of the staple pushing bar; the safety mechanism further comprises a floating block displaceable in the second half-section in an up-down direction perpendicular to a length direction of the second half-section; in a first state, the engaging member is engaged with the notch, to stop the staple pushing bar from moving forward in the length direction of the second half-section; and in a second state, the floating block abuts against the staple cartridge or a staple anvil to drive a top end of the engaging member that is towards the first half-section to displace downwards in the up-down direction perpendicular to the length direction of the second half-section, the engaging member is disengaged from the notch, to allow the staple pushing bar to move forward in the length direction of the second half-section; and
    a bottom end of the floating block that is away from the first half-section is connected to the top end of the engaging member that is towards the first half-section, a bottom end of the engaging member that is away from the first half-section is connected to the second half-section, and a first through slot and a second through slot for the staple pushing bar and the cutter pushing bar to pass through respectively are provided on the floating block in the length direction of the second half-section.

2. The linear cutting stapler according to claim 1, wherein a protrusion to be pressed by the staple cartridge is provided at an end of the floating block towards the staple cartridge, and wherein by pressing the protrusion, the staple cartridge drives the top end of the engaging member to displace downwards in the up-down direction perpendicular to the length direction of the second half-section, so that the engaging member is disengaged from the notch.

3. The linear cutting stapler according to claim 2, wherein the engaging member is a leaf spring with a bottom end being away from the first half-section and welded to an inner wall of the second half-section, and a top end being towards the first half-section and fixedly connected to the floating block.

4. The linear cutting stapler according to claim 2, wherein the engaging member is connected to a center of a bottom surface of the second half-section that is away from the first half-section, and the notch is correspondingly arranged at a center of a bottom surface of the staple pushing bar that is away from the first half-section.

5. The linear cutting stapler according to claim 1, wherein a protrusion to be pressed by the staple anvil is provided at an end of the floating block towards the staple anvil, and wherein by pressing the protrusion, the staple anvil drives the top end of the engaging member to displace downwards in the up-down direction perpendicular to the length direction of the second half-section, so that the engaging member is disengaged from the notch.

6. The linear cutting stapler according to claim 5, wherein the engaging member is a leaf spring with a bottom end being away from the first half-section and welded to an inner wall of the second half-section, and a top end being towards the first half-section and fixedly connected to the floating block.

7. The linear cutting stapler according to claim 5, wherein the engaging member is connected to a center of a bottom surface of the second half-section that is away from the first half-section, and the notch is correspondingly arranged at a center of a bottom surface of the staple pushing bar that is away from the first half-section.

8. The linear cutting stapler according to claim 1, wherein the engaging member is a leaf spring with a bottom end being away from the first half-section and welded to an inner wall of the second half-section and a top end being towards the first half-section and fixedly connected to the floating block.

9. The linear cutting stapler according to claim 1, wherein the engaging member is an engaging block at a bottom portion of the floating block that is away from the first half-section, a top end of the engaging block that is towards the first half-section is engaged with the notch, and a bottom end of the engaging block that is away from the first half-section is connected to a bottom surface of the second half-section that is away from the first half-section by a spring, and wherein when the floating block abuts against the staple cartridge or the staple anvil to drive the engaging member to displace downwards in the up-down direction perpendicular to the length direction of the second half-section, a bottom portion of the engaging member that is away from the first half-section is disengaged from the notch.

10. The linear cutting stapler according to claim 9, wherein the engaging block and the floating block are manufactured integrally.

11. The linear cutting stapler according to claim 1, wherein the engaging member is connected to a center of a bottom surface of the second half-section that is away from the first half-section, and the notch is correspondingly arranged at a center of a bottom surface of the staple pushing bar that is away from the first half-section.

12. The linear cutting stapler according to claim 1, wherein the floating block comprises a first side having a first protrusion and a second side opposite the first side with respect to a width direction, the second side of the floating block has a second protrusion, and the second half-section comprises a first inner sidewall having a first groove and a second inner sidewall opposite the first inner sidewall with respect to the width direction, the second inner sidewall has a second groove, wherein the width direction is oriented perpendicular to the length direction of the second half-section, and the width direction is also perpendicular to the up-down direction perpendicular to the length direction of the second half-section, and the first protrusion is fittingly movable within the first groove and the second protrusion is fittingly movable within the second groove in the up-down direction perpendicular to the length direction of the second half-section.

* * * * *